(12) United States Patent
Kucmierczyk et al.

(10) Patent No.: US 11,008,275 B2
(45) Date of Patent: May 18, 2021

(54) PROCESS FOR PREPARING CARBOXYLIC ACIDS OR SALTS THEREOF FROM HYDROCARBONS

(71) Applicant: Evonik Operations GmbH, Essen (DE)

(72) Inventors: Peter Kucmierczyk, Herne (DE); Robert Franke, Marl (DE); Dirk Fridag, Haltern am See (DE); Johannes Knossalla, Schermbeck (DE); Marc Schäpertöns, Recklinghausen (DE); Frederik Gluth, Mülheim an der Ruhr (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 16/893,481

(22) Filed: Jun. 5, 2020

(65) Prior Publication Data

US 2020/0392062 A1    Dec. 17, 2020

(30) Foreign Application Priority Data

Jun. 12, 2019 (EP) .................................... 19179571

(51) Int. Cl.
| | | |
|---|---|---|
| C07C 51/09 | (2006.01) | |
| C07C 51/41 | (2006.01) | |
| B01D 61/24 | (2006.01) | |
| B01D 61/02 | (2006.01) | |
| C07C 67/38 | (2006.01) | |
| B01D 3/14 | (2006.01) | |
| C07C 67/02 | (2006.01) | |

(52) U.S. Cl.
CPC ............. *C07C 51/09* (2013.01); *B01D 3/145* (2013.01); *B01D 61/027* (2013.01); *B01D 61/246* (2013.01); *C07C 51/41* (2013.01); *C07C 67/02* (2013.01); *C07C 67/38* (2013.01); *B01D 2311/2669* (2013.01)

(58) Field of Classification Search
CPC ......... C07C 51/09; C07C 51/41; C07C 67/03; C07C 67/38; B01D 61/027; B01D 61/246; B01D 3/145
See application file for complete search history.

(56) References Cited

U.S. PATENT DOCUMENTS

| | | | |
|---|---|---|---|
| 5,892,119 A * | 4/1999 | Bryant .................... C07C 45/50 568/451 |
| 6,800,783 B2 | 10/2004 | Springer et al. | |
| 7,799,945 B2 | 9/2010 | Springer | |
| 8,748,643 B2 * | 6/2014 | Priske .................. B01J 31/4061 556/13 |
| 9,334,227 B2 * | 5/2016 | Eastham ................. C07C 67/38 |
| 9,676,805 B2 | 6/2017 | Dyballa et al. | |
| 9,688,604 B2 | 6/2017 | Jennerjahn et al. | |
| 9,725,398 B2 * | 8/2017 | Dong ....................... B01J 31/24 |
| 9,845,276 B2 | 12/2017 | Franke et al. | |
| 10,077,228 B2 | 9/2018 | Dong et al. | |
| 10,155,200 B2 | 12/2018 | Geilen et al. | |
| 10,202,329 B2 | 2/2019 | Dong et al. | |
| 10,245,578 B2 | 4/2019 | Klasovsky et al. | |
| 10,294,191 B2 | 5/2019 | Dong et al. | |
| 10,501,392 B2 | 12/2019 | Fridag et al. | |
| 10,562,833 B2 | 2/2020 | Fridag et al. | |
| 10,577,297 B2 | 3/2020 | Fridag et al. | |
| 10,633,302 B2 | 4/2020 | Nadolny et al. | |
| 10,647,650 B2 | 5/2020 | Hecht et al. | |
| 10,654,784 B2 | 5/2020 | Hasselberg et al. | |
| 2006/0128985 A1 | 6/2006 | Eastham et al. | |
| 2009/0012323 A1 | 1/2009 | Van Rensburg et al. | |
| 2016/0236150 A1 * | 8/2016 | Geilen ................. B01J 31/4061 |
| 2016/0257634 A1 | 9/2016 | Dyballa et al. | |
| 2017/0022138 A1 | 1/2017 | Dong et al. | |
| 2019/0283003 A1 | 9/2019 | Nadolny et al. | |
| 2019/0283004 A1 | 9/2019 | Nadolny et al. | |
| 2019/0283005 A1 | 9/2019 | Nadolny et al. | |

FOREIGN PATENT DOCUMENTS

| | | | |
|---|---|---|---|
| DE | 100 10 771 C1 | 5/2001 | |
| EP | 1 854 778 A1 | 11/2007 | |
| EP | 3 121 184 A2 | 1/2017 | |
| WO | 2013/107902 A1 | 7/2013 | |
| WO | WO 2013/017902 * | 7/2013 | ............. C07C 67/38 |
| WO | 2015/110843 A1 | 7/2015 | |

OTHER PUBLICATIONS

Kucmierczyk et al., U.S. Appl. No. 16/893,481, filed Jun. 5, 2020.
Kucmierczyk et al., U.S. Appl. No. 16/888,920, filed Jun. 1, 2020.
Kucmierczyk et al., U.S. Appl. No. 16/888,925, filed Jun. 1, 2020.
European Search Report dated Dec. 10, 2019 in EP 19179571.5 (6 pages).
Marchetti et al., "Molecular Separation with Organic Solvent Nanofiltration: A Critical Review", Chemical Reviews, Bd. 114, Nr. 21, Copyright Oct. 2014, pp. 10735-10806 (72 pages).

\* cited by examiner

*Primary Examiner* — Yate' K Cutliff
(74) *Attorney, Agent, or Firm* — Taylor English Duma LLP; Philip P. McCann

(57) ABSTRACT

The invention relates to a process for preparing carboxylic acids or salts thereof by hydrolysis or saponification of an ester, which is obtained by alkoxycarbonylation of a C2 to C20 hydrocarbon having at least one multiple bond, preferably having at least one olefinic double bond, in which the homogeneous catalyst system used is separated from the product mixture by means of membrane separation. In a development of the present invention, the ester thus formed is converted into another ester by transesterification and then hydrolyzed or saponified.

19 Claims, No Drawings

PROCESS FOR PREPARING CARBOXYLIC ACIDS OR SALTS THEREOF FROM HYDROCARBONS

CROSS REFERENCE TO RELATED APPLICATIONS

This application is a 35 U.S.C. § 119 patent application which claims the benefit of European Application No. 19179571.5 filed Jun. 12, 2019, which is incorporated herein by reference in its entirety.

FIELD

The present invention relates to a process for preparing carboxylic acids or salts thereof by hydrolysis or saponification of an ester, which is obtained by alkoxycarbonylation of a C2 to C20 hydrocarbon having at least one multiple bond, preferably having at least one olefinic double bond, in which the homogeneous catalyst system used is separated from the product mixture by means of membrane separation. In a development of the present invention, the ester thus formed is converted into another ester by transesterification and then hydrolyzed or saponified.

BACKGROUND

The production of alcohols in large-scale industrial chemistry is achieved largely by hydroformylation to produce an aldehyde, with subsequent oxidation of the aldehyde to the carboxylic acid. Although the production of carboxylic acids through hydroformylation with subsequent oxidation has been an industrially established and proven process for decades, there is still potential for improvement (cf. DE 100 10 771 C1 or EP 1 854 778 A1). One problem with this synthetic route is that catalyst systems containing transition metals are used in the hydroformylation, which are usually expensive or have to be produced at considerable cost. Another problem is the formation of by-products, which can be observed even when no catalyst is used and/or the reaction conditions are relatively mild. A further problem is the increased need for safety equipment in the oxidation of aldehydes, since this step involves oxygen in pure form or through air being supplied to the organic reaction mixture. The resulting explosive atmosphere must be monitored and regulated separately and with difficulty.

To avoid side reactions and to increase the selectivity, the addition of alkali metal compounds and/or alkaline earth metal compounds to the reaction solution has been proposed in the literature. However, a disadvantage of this variant is that these compounds have an inhibitory effect on the oxidation of the aldehydes, which means that longer reaction times are necessary in order to achieve adequate conversions.

SUMMARY

The object underlying the present invention was therefore to specify an alternative synthetic route for preparing carboxylic acid or salts thereof with which the desired carboxylic acids or salts thereof can be accessed relatively easily and in which there is no need for the presence of alkali metal compounds and/or alkaline earth metal compounds. A further important objective is that the manufacturing process can be carried out on a large industrial scale. Central to this is the replacement of the classic synthesis by a different synthesis technology that provides the products of the known process in better quality. In addition, the novel synthetic route to be established should give rise to fewer unwanted by-products. The additional safety equipment that is necessary because of the presence of oxygen should additionally be reduced.

This object is achieved by a two-stage process in which, in a first step, a hydrocarbon having at least one multiple bond undergoes a alkoxycarbonylation reaction with carbon monoxide and an alcohol to form an ester and, in a second step, the ester undergoes a hydrolysis or saponification reaction in the presence of an acidic catalyst or a saponifying agent to form the desired carboxylic acid or the desired carboxylic acid salt. In the second step of this process, some of the alcohol originally used is released again.

DETAILED DESCRIPTION

According to the invention, the process for preparing a carboxylic acid or the salt thereof comprises the following steps:

a) preparing an ester by reacting (carbonylating) a C2 to C20 hydrocarbon having at least one multiple bond, preferably having at least one olefinic double bond, with carbon monoxide and with an alcohol A in the presence of a homogeneous catalyst system in a reaction zone to obtain a product mixture;

b) carrying out a membrane separation to separate the homogeneous catalyst system from the product mixture, whereby the homogeneous catalyst system and unreacted hydrocarbon and/or unreacted alcohol A, preferably unreacted alcohol A, are enriched in the retentate and the ester formed in step a) is enriched in the permeate, wherein the membrane material used is a membrane material capable of OSN (organic solvent nanofiltration) that includes at least one separation-active layer;

c) separating the ester formed in step a) from the permeate in at least one separation step selected from thermal separation, for example distillation, extraction, crystallization and membrane separation;

d) hydrolysing or saponifying the ester prepared in step a) in the presence of an acidic catalyst or a saponifying agent to obtain a reaction mixture that comprises at least the carboxylic acid or salt thereof, the eliminated alcohol A, water and unreacted ester;

e) separating the carboxylic acid or salt thereof formed in step d) in at least one separation process step selected from thermal separation, for example distillation, extraction, crystallization and membrane separation.

The hydrocarbons used in the reaction in step a) must have at least one multiple bond. Preference is given to hydrocarbons having at least one olefinic double bond and particular preference to hydrocarbons having one olefinic double bond. There is in principle no limit to the number of carbon atoms in the compound having at least one multiple bond, preferably at least one olefinic double bond. However, only the carbonylation of C2 to C20 hydrocarbons having at least one multiple bond, preferably at least one olefinic double bond, is industrially relevant. In a preferred embodiment of the present invention, C3 to C16 hydrocarbons, more preferably C3 to C12 hydrocarbons, having at least one multiple bond, preferably at least one olefinic double bond, may be used. These include in particular n-alkenes, isoalkenes, cycloalkenes and aromatic alkenes having 2 to 20 carbon atoms, preferably 3 to 16 carbon atoms, more preferably 3 to 12 carbon atoms.

The hydrocarbons described above may contain one or more further functional groups in addition to the at least one olefinic double bond. Examples of suitable functional groups are carboxyl, thiocarboxyl, sulfo, sulfinyl, carboxylic anhydride, imide, carboxylic ester, sulfonic ester, carbamoyl, sulfamoyl, cyano, carbonyl, carbonothioyl, hydroxyl, sulfhydryl, amino, ether, thioether, aryl, heteroaryl or silyl groups and/or halogen substituents.

Particularly preferred hydrocarbons used in step a) of the process according to the invention have only one olefinic double bond, in particular n-alkenes and isoalkenes having 2 to 20 carbon atoms, preferably 3 to 16 carbon atoms, more preferably 3 to 12 carbon atoms. The hydrocarbons used are preferably unsubstituted.

The employed and above-described hydrocarbons are according to the invention reacted in step a) with carbon monoxide (CO) and an alcohol to form the corresponding ester. The carbon monoxide may be provided directly as a feed mixture or by adding a carbon monoxide-containing gas selected from synthesis gas, water gas, generator gas and other carbon monoxide-containing gases. It is also possible to provide the carbon monoxide by first separating the carbon monoxide-containing gas into its components in a manner known to those skilled in the art and passing the carbon monoxide into the reaction zone. The carbon monoxide may still contain a certain proportion of hydrogen or other gases, because complete separation is almost impossible.

The alcohol used in the reaction in step a) is a mono- or polyol (two or more OH groups) having 1 to 50 carbon atoms, preferably 1 to 15 carbon atoms, more preferably 1 to 10 carbon atoms, or a mixture of two or more mono- and/or polyols. In a preferred embodiment, the polyol is a diol, triol or tetraol, preferably a diol or triol having the abovementioned number of carbon atoms.

Suitable alcohols for the reaction in step a) are methanol, ethanol, 1-propanol, 1-butanol, 1-pentanol, 1-hexanol, 2-propanol, tert-butanol, 3-pentanol, 2-propylheptanol, cyclohexanol, phenol or mixtures thereof, preferably ethanol, 1-propanol, 1-butanol, 1-pentanol, 1-hexanol, 2-propanol, tert-butanol, 3-pentanol, 2-propylheptanol.

The alcohol used in step a) is preferably used in a molar ratio to the hydrocarbon used (alcohol:hydrocarbon) of 2 to 20, more preferably 3 to 10 and particularly preferably 4 to 6. The monool is thus added in a molar excess based on the hydrocarbon used. The alcohol may accordingly serve both as a reactant for the carbonylation and as solvent. The alcohol used in step a), when it is a polyol, is used in a molar ratio to the hydrocarbon used (hydrocarbon:polyol) of 2 to 20, preferably of 3 to 10 and more preferably of 4 to 8. The polyol is thus added in a molar deficit based on the hydrocarbon used.

The reaction according to the invention in step a) is carried out in the presence of a homogeneous catalyst system. The homogeneous catalyst system preferably comprises at least one metal from groups 8 to 10 of the periodic table of the elements (PTE) or a compound thereof, a phosphorus-containing ligand and an acid as co-catalyst.

The metal from groups 8 to 10 of the PTE is preferably palladium. The palladium is preferably used in the form of a precursor compound as a palladium compound coordinated by the phosphorus-containing ligand. Examples of palladium compounds that may be used as precursor compounds are palladium chloride [$PdCl_2$], palladium(II) acetylacetonate [$Pd(acac)_2$], palladium(II) acetate [$Pd(OAc)_2$], dichloro(1,5-cyclooctadiene)palladium(II) [$Pd(cod)Cl_2$], bis(dibenzylideneacetone)palladium(0) [$Pd(dba)_2$], tris(dibenzylideneacetone)dipalladium(0) [$Pd_2(dba)_3$] bis(acetonitrile)dichloropalladium(II) [$Pd(CH_3CN)_2Cl_2$], palladium (cinnamyl)dichloride [$Pd(cinnamyl)Cl_2$]. Preference is given to using the compounds [$Pd(acac)_2$] or [$Pd(OAc)_2$]. The concentration of palladium metal in step a) is preferably between 0.01 and 0.6 mol %, preferably between 0.03 and 0.3 mol %, more preferably between 0.04 and 0.2 mol %, based on the molar amount of the hydrocarbon used.

Suitable phosphorus-containing ligands of the catalyst system according to the invention preferably have a bidentate structure. Preferred phosphorus-containing ligands for the catalyst system according to the invention are benzene-based diphosphine compounds, as disclosed, for example, in EP 3 121 184 A2. The ligands may be combined with the palladium in a preliminary reaction so that the palladium-ligand complex is fed into the reaction zone or added to the reaction in situ and combined with the palladium there. The molar ratio of ligand to metal for the reaction described in step a) may be 1:1 to 10:1, preferably 2:1 to 6:1, more preferably 3:1 to 5:1.

The homogeneous catalyst system further comprises an acid, in particular a Brønsted acid or a Lewis acid. Lewis acids used may in particular be Lewis acids having an LAU value of more than 25, preferably having an LAU value of 29. The LAU value is a method for determining the strength of Lewis acids (J R Gaffen et al., Chem, vol. 5, issue 6, p. 1567-1583). Lewis acids used are preferably aluminium triflate, aluminium chloride, aluminium hydride, trimethylaluminium, tris(pentafluorophenyl)borane, boron trifluoride, boron trichloride or mixtures thereof. Of the Lewis acids mentioned, preference is given to using aluminium triflate. The Lewis acid is preferably added in a molar ratio of Lewis acid to ligand of 1:1 to 20:1, preferably 2:1 to 15:1, more preferably 5:1 to 10:1.

Suitable Brønsted acids preferably have an acid strength pKa of ≤5, more preferably an acid strength pKa of ≤3. The stated acid strength pKa refers to the pKa determined under standard conditions (25° C., 1.01325 bar). For polyprotic acids, the acid strength pKa in the context of this invention relates to the pKa of the first protolysis step. The Brønsted acid is preferably added in a molar ratio of Brønsted acid to ligand of 1:1 to 15:1, preferably 2:1 to 10:1, more preferably 3:1 to 4:1.

The Brønsted acid used may in particular be perchloric acid, sulfuric acid, phosphoric acid, methylphosphonic acid or sulfonic acids. Examples of suitable sulfonic acids are methanesulfonic acid, trifluoromethanesulfonic acid, tert-butanesulfonic acid, p-toluenesulfonic acid (PTSA), 2-hydroxypropane-2-sulfonic acid, 2,4,6-trimethylbenzenesulfonic acid and dodecylsulfonic acid. Particularly preferred acids are sulfuric acid, methanesulfonic acid, trifluoromethanesulfonic acid and p-toluenesulfonic acid. The acid is preferably sulfuric acid.

The reaction/carbonylation in step a) of the employed hydrocarbon having an olefinic double bond is preferably carried out at a temperature of 25 to 140° C., more preferably at a temperature of 80 to 130° C. and particularly preferably at a temperature of 90 to 120° C. The pressure in step a) may be between 5 and 60 bar, preferably between 10 and 40 bar, more preferably between 15 and 30 bar.

The described reaction in step a) takes place in a suitable reaction zone. The reaction zone for the reaction comprises at least one reactor, but may also consist of two or more reactors. The at least one reactor may in particular be selected from the group consisting of a stirred-tank reactor, a loop reactor, a jet-loop reactor, a bubble-column reactor or combinations thereof. If more than one reactor is used, the reactors may be identical or different.

The reaction in step a) described above affords a liquid product mixture that comprises at least the ester formed by the reaction, the homogeneous catalyst system, unreacted alcohols A, and any further components such as low boilers, for example low-boiling by-products such as ethers, and/or high boilers and/or unreacted hydrocarbons. The product mixture is then fed into the subsequent membrane separation in step b). In the reaction in step a), an offgas that consists at least of unreactive impurities such as nitrogen, hydrogen and low-boiling by-products (for example the ethers already mentioned) may also be removed from the reaction zone. The impurities and low-boiling by-products could accumulate and, over time, lower the partial pressure of the reaction gas (CO), thereby slowing down the reaction.

In step b) that follows, the product mixture is fed into a membrane separation to separate the homogeneous catalyst system from the product mixture. The membrane material according to the invention causes enrichment in the retentate of the homogeneous catalyst system and unreacted hydrocarbon and/or unreacted alcohol, whereas the ester formed in step a) is enriched in the permeate. The permeate containing the formed ester is then supplied to the subsequent step c).

The retentate containing the enriched homogeneous catalyst system is then recycled into the reaction zone. On recycling the retentate, a purge stream that may contain inert alkanes, low-boiling by-products (for example ethers), possible decomposition products of the catalyst system or other impurities introduced by the hydrocarbon streams used, for example traces of water or nitrogen, may additionally be removed to avoid accumulation in the reaction zone(s). The recycling of the retentate ensures that the catalyst system obtained in the retentate in the membrane separation is returned to the reaction. This minimizes catalyst losses through deposition or deactivation and makes the process more cost-efficient. Catalyst losses usually cannot be avoided entirely, but the effect of the decrease in the losses mentioned is that less catalyst has to be replaced by supply of fresh catalyst.

Membrane separation is based on the semipermeability of the membrane material, which is permeable to certain substances and impermeable to others. The membrane material used in step b) of the process according to the invention is an OSN membrane material (OSN=organic solvent nanofiltration). Such a membrane material preferably consists at least of a relatively thin separation-active layer (also: active separation layer) and optionally a thicker backing on which the separation-active layer is located. The membrane material according to the invention preferably consists at least of a separation-active layer and a backing. One or more intermediate layers may be present between the separation-active layer and the backing. In a preferred embodiment, the membrane material consists solely of the separation-active layer and the backing. The membrane material, comprising at least the separation-active layer and backing, is preferably acid-stable so that the membrane material is not damaged by the acid present in the product mixture as a co-catalyst. In the context of the present invention, the term "acid stable" means that, in the presence of the acid in the catalyst system, in particular a Brnsted acid having a pKa≤5, more preferably having a pKa≤3, or a Lewis acid having an LAU value of more than 25, preferably having an LAU value of 29, the membrane material is stable for at least 300 h without being destroyed and thereby being no longer able to achieve the actual separation effect.

In particular, the backing has a porous structure that is permeable to the permeate that has passed through the separation-active layer. The backing has a stabilizing function and serves as a support for the separation-active layer. The backing may in principle be composed of any suitable porous material. A prerequisite, however, is that the material is acid-stable. The backing may also be composed of the same material as the separation-active layer.

The separation-active layer according to the invention is preferably composed of a PAEK (polyaryl ether ketone) polymer. PAEK has the particular feature that, within the repeat unit, aryl groups are linked alternately via an ether functionality and a ketone functionality. A separation-active layer which is preferred according to the invention is composed of PEEK (polyether ether ketone). As the separation-active layer, particular preference is given to using PEEK polymers having a degree of sulfonation of less than 20%, particularly preferably having a degree of sulfonation of less than 10%. The corresponding PEEK polymers and the preparation thereof are described in WO 2015/110843 A1. This material has surprisingly been found to be particularly stable, particularly also towards the acid co-catalyst of the homogeneous catalyst system. In addition, a particular feature of the PEEK material according to the invention is that, when used as a separation-active layer, it allows the esters that are formed to pass through preferentially, whereas even the alcohols used as reactants are at least partially retained and thereby accumulate in the retentate. This allows the subsequent processing of the residual product mixture to be carried out more economically and for longer, because less alcohol needs to be removed compared with known membrane materials.

The membrane separation in step b) is carried out preferably at a temperature of 25 to 100° C., more preferably 30 to 80° C. and particularly preferably 40 to 70° C. To bring the product mixture to the prevailing temperature preferred for the membrane separation, the product mixture may be cooled. In addition to active cooling using a coolant, cooling may also be achieved via a heat exchanger, whereby another stream is heated within the process according to the invention. There is also optionally a degassing step between the reaction zone in step a) and the membrane separation in step b) for preliminary removal from the product mixture of highly volatile compounds such as carbon monoxide and/or residual unreactive impurities that have not been removed via the offgas, such as nitrogen, hydrogen, alkanes and low-boiling by-products (for example the ethers already mentioned). The product mixture is first depressurized below the partial pressure of the dissolved components, such as carbon monoxide, so that they are displaced from solution, thereby allowing the pressure to then be raised again as specified for the membrane separation.

The transmembrane pressure (TMP) in step b) may be 10 to 60 bar, preferably 15 to 55 bar, more preferably 20 to 50 bar (relative). The permeate-side pressure may here be above atmospheric pressure up to 15 bar, preferably 3 to 7 bar, which then gives rise to the retentate-side pressure brought about by the TMP. In a preferred embodiment, care should be taken, in the case of the pressure ratios and the permeate-side pressure in particular, to ensure that the pressure is set according to the hydrocarbon used, the alcohol used and the temperature in the system, in order to avoid evaporation after passage through the membrane, since this could make the entire operation unstable. The same applies in principle also to dissolved components such as carbon monoxide, which may optionally be removed by the degassing step already mentioned.

In the subsequent step c), to separate the esters formed in step a) from the remaining permeate, the permeate from the membrane separation (step b)) is subjected to a separation process selected from the group consisting of a thermal separation, for example distillation, extraction, crystallization or a further membrane separation. The separation process is preferably a distillation. The appropriate process conditions are known to those skilled in the art.

In the separation process used in step c) and in the distillation in particular, there is the possibility that this separates from the permeate not just the ester that is formed, but the possibly resulting high boilers too, for example high-boiling by-products that may arise in the reaction in step a). In order to remove these high boilers, the process according to the invention may include a purification step, i.e. a step in which the ester formed is purified by separating the ester from high boilers present in the permeate by means of a thermal separation, extraction, crystallization or membrane separation. Preferably a thermal separation process, more preferably a further distillation, is used to purify the esters formed. The process conditions are known to those skilled in the art.

In a preferred embodiment, the permeate obtained in step c), which is largely free of the ester formed in step a) and comprises at least unreacted alcohols and/or unreacted hydrocarbons, undergoes a separation of recyclable components. In this separation, the unreacted alcohols and/or unreacted hydrocarbons are separated from the remaining permeate, in particular from the low boilers contained therein, by means of a thermal separation, extraction, crystallization or membrane separation. Preferably a thermal separation process, more preferably a further distillation, is used to separate the unreacted alcohols and/or unreacted hydrocarbons from the remaining permeate. The process conditions are known to those skilled in the art. The unreacted alcohols and/or unreacted hydrocarbons thereby obtained may then be recycled into the reaction zone.

The ester formed by the process according to the invention may be transesterified in two further process steps c1) and c2). In this transesterification, the part of the ester that corresponds to the first alcohol A used in step a) is replaced by a second alcohol B. This transesterification is carried out after step c) mentioned above, optionally after the possible purification step, and comprises the following steps:

c1) transesterifying the ester formed in step a) with a second alcohol B, wherein this second alcohol differs from the alcohol A used in step a), in a second reaction zone to obtain a second product mixture that comprises at least the ester with the second alcohol B, the eliminated first alcohol A and unreacted second alcohol B;

c2) separating the ester formed with the second alcohol B from the rest of the second product mixture and in particular from the eliminated first alcohol A through thermal separation and/or by means of membrane separation, and recycling the eliminated first alcohol A into the reaction zone from step a) and also recycling the unreacted alcohol B into the second reaction zone.

Step c1) is where the actual transesterification takes place, that is to say the elimination of the first alcohol A actually attached in step a) and the attachment of the second alcohol B. In this step, the ester formed in step a) is reacted in a reaction zone with a second alcohol B that differs from the first alcohol A. In a particularly preferred embodiment, the second alcohol B used in the transesterification is a higher-boiling alcohol compared with the first alcohol A used in step a). In order to favor the transesterification reaction, the second alcohol B is preferably added in excess in the transesterification.

The second alcohol used in the transesterification in step c1) is preferably a mono- or polyol (two or more OH groups) having 1 to 50 carbon atoms, more preferably having 1 to 15 carbon atoms, particularly preferably having 1 to 10 carbon atoms, or a mixture of two or more mono- and/or polyols, with the proviso that the first alcohol A used in step a) and the second alcohol B are non-identical. In a preferred embodiment, the polyol is a diol, triol or tetraol, preferably a diol or triol having the abovementioned number of carbon atoms. Suitable alcohols for the reaction in step a) are methanol, ethanol, 1-propanol, 1-butanol, 1-pentanol, 1-hexanol, 2-propanol, tert-butanol, 3-pentanol, 2-propylheptanol, cyclohexanol, phenol, pentaerythritol, neopentyl glycol, trimethylolpropane, dipentaerythritol or mixtures thereof, preferably ethanol, 1-propanol, 1-butanol, 1-pentanol, 1-hexanol, 2-propanol, tert-butanol, 3-pentanol, 2-propylheptanol.

The transesterification in step c1) is preferably carried out under acid or base catalysis. The acids used may be Brønsted or Lewis acids.

Suitable Brønsted acids for the transesterification in step c1) are perchloric acid, sulfuric acid, phosphoric acid, methylphosphonic acid or a sulfonic acid, for example methanesulfonic acid, trifluoromethanesulfonic acid, tert-butanesulfonic acid, p-toluenesulfonic acid (pTSA), 2-hydroxypropane-2-sulfonic acid, 2,4,6-trimethylbenzenesulfonic acid or dodecylsulfonic acid. The Brønsted acid used is preferably sulfuric acid or a sulfonic acid, more preferably sulfuric acid. Metal or compounds thereof may also be used, for example tin powder, tin(II) oxide, tin(II) oxalate, titanic esters such as tetraisopropyl orthotitanate or tetrabutyl orthotitanate and also zirconium esters such as tetrabutyl zirconate and also sodium methoxide and potassium methoxide.

Suitable Lewis acids for the transesterification in step c1) are titanium(IV) isopropoxide, $Bu_2SnO$, BuSn(O)OH or aluminium triflate. Preference is given to using titanium(IV) isopropoxide and aluminium triflate as Lewis acids.

Suitable bases for the transesterification in step c1) are alkali metals, alkali metal alkoxides, alkali metal or alkaline earth metal acetates or oxides, alkali metal or alkaline earth metal alkoxides such as NaEtOH or MgEtOH, or alkali metal carbonates such as $K_2CO_3$ or $Cs_2CO_3$. Basic ion exchangers or NaOH may, however, also be used. Preference is given to using Na or Mg alkoxides, such as NaEtOH or MgEtOH.

The acid-catalyzed transesterification is preferably carried out at a temperature from 60 to 220° C., more preferably from 100 to 210° C. and particularly preferably at 130 to 200° C. The reaction preferably takes place above the boiling point of the first alcohol A to be eliminated so as to remove the eliminated first alcohol A directly from the reaction mixture and thus promote a shift in equilibrium to the product side. The second alcohol B is preferably added to the ester formed in step a) in a significant excess, for example 30:1.

The base-catalyzed transesterification takes place preferably at a temperature of 20 to 100° C.

The described transesterification affords a second product mixture comprising at least the ester with the second alcohol B, the eliminated first alcohol A and unreacted second alcohols B.

The second ester formed in step c1) is separated from the remaining second product mixture in the subsequent step c2). The separation is carried out by means of a thermal separation, preferably distillation, and/or by means of membrane separation, in particular using the membrane materials described above. The appropriate process conditions are known to those skilled in the art.

In the separation process used in step c2) and in the distillation in particular, there is the possibility that this separates from the rest of the second product mixture not just the ester that is formed, but possibly formed high boilers too, for example high-boiling by-products that may arise in the reaction in step c1). In order to remove these high boilers, the process according to the invention may include a purification step, i.e. a step in which the ester formed in step c1) is purified by separating the ester from the high boilers present by means of a thermal separation, extraction, crystallization or membrane separation. Preferably a thermal separation process, more preferably a further distillation, is used to purity the esters formed. The process conditions are known to those skilled in the art.

The ester prepared in step a) and separated from the permeate in step c) and optionally purified then undergoes a hydrolysis or saponification in step d). The ester group is cleaved by the acidic catalyst employed in the process or by the saponifying agent employed in this process, resulting in the formation of a carboxylic acid or carboxylate salt and allowing the alcohol A bound in the ester formation in step a) or the alcohol B bound in the transesterification to be recovered. The saponification accordingly gives rise to a reaction mixture that comprises at least the carboxylic acid or salt thereof, alcohol A or B and unreacted esters.

Without transesterification, the alcohol A recovered with the hydrolysis or saponification in step d) can be separated from the resulting alcohol mixture in a subsequent process step and recycled into the first reaction zone. If a transesterification has been carried out with recovery of the alcohol B in the hydrolysis or saponification in step d), this subsequent process step can be separated from the reaction mixture formed and recycled into the second reaction zone.

The hydrolysis is a known chemical reaction in which an ester is converted with the aid of an acidic catalyst into a carboxylic acid with elimination of an alcohol. The typical conditions in the hydrolysis are known to those skilled in the art.

The hydrolysis in step d) takes place in the presence of an acidic heterogeneous or homogeneous catalyst. Known homogeneous catalysts are acidic compounds such as Brønsted acids, in particular HCl, $H_2SO_4$, phosphoric acid, p-toluenesulfonic acid and 4-dodecylbenzenesulfonic acid, or Lewis acids, in particular $AlCl_3$, $ZnCl_2$, $HfCl_4 \cdot 2THF$, $Al(OTf)_3$. Known heterogeneous catalysts are acidic compounds such as cation exchangers, acidic H-zeolites, acidic functionalized metal oxides with silica and heteropolyacids. Suitable heterogenous catalysts are in particular Amberlyst® 15, Amberlyte® IR 120 (H), $HCl_4$-$SiO_2$, 3-propylsulfonic acid-functionalized silica, Nafion®-$SiO_2$, Aciplex®-$SiO_2$, $Cs_{2.5}H_{0.5}PW_{12}O_{40}$, H-ZSM5, H-ZSM-5-C18, Z-beta-H-25, Z-beta-H-38, Z-beta-H-150, Z-beta-H-360, Z-Y-H-60, Z-Y-H-80.

In the subsequent step e), to separate the carboxylic acid or the salt thereof formed in step d) from the rest of the reaction mixture, the reaction mixture from the hydrolysis in step d) is subjected to at least one separation process step selected from the group consisting of a thermal separation, for example distillation, an extraction, a crystallization or a further membrane separation. The separation process is preferably a distillation. The appropriate process conditions are known to those skilled in the art. A multistep distillation may also be carried out.

Saponification is a known chemical reaction in which an ester is converted with the aid of a basic or enzymatic saponifying agent into a carboxylic acid salt with elimination of an alcohol. The typical conditions during the saponification are known to those skilled in the art The saponification in step d) takes place in the presence of a saponifying agent. Known saponifying agents are basic compounds such as potassium hydroxide, potassium (hydrogen) carbonate, sodium hydroxide, sodium (hydrogen) carbonate or amine compounds. Also possible is saponification with an enzymatic saponifying agent, in particular esterases.

In the subsequent step e), to separate the carboxylic acid salt formed in step d) from the rest of the reaction mixture, the reaction mixture from the saponification in step d) is subjected to at least one separation process step selected from the group consisting of a thermal separation, for example distillation, an extraction, a crystallization or a further membrane separation. The separation process is preferably a distillation. The appropriate process conditions are known to those skilled in the art. A multistep distillation may also be carried out.

In the at least one separation process step, the alcohols A and B used may additionally also be removed and recycled into the first or second reaction zone respectively. During recycling, a purge stream may be withdrawn, for example in order to discharge by-products from the process.

Example 1

Conversion of diisobutene (DiB) to the corresponding ester methyl 3,5,5-trimethylhexanoate (TMH ester) and subsequent hydrolysis to 3,5,5-trimethylhexanoic acid (TMH acid). The diisobutene is a mixture consisting of the two C8 isomers 2,4,4-trimethylpent-1-ene and 2,4,4-trimethylpent-2-ene in ratios of about 80:20.

A 200 ml glass autoclave from Büchi was closed and to displace oxygen it was alternately (3×) pressurized with argon to 10 bar and then the excess pressure released. The following were weighed under argon into a secured Schlenk flask [Pd(acac)$_2$] (76.37 mg; 0.06 mol % based on DiB), 1,2-bis((tert-butyl(pyridin-2-yl)phosphanyl)methyl)benzene (218 mg; 0.12 mol % based on DiB), MeOH (84 mL; 500 mol % based on DiB), $H_2SO_4$ (147 mg; 0.36 mol % based on DiB), DiB (65.6 mL, 0.41 mol). The solution was transferred to the autoclave by means of a connecting tube and argon overpressure and the autoclave was closed. After venting the argon, this was pressurized to 10 bar with CO. The autoclave is stirred at 500 rpm and heated with an oil bath to 120° C. (with regulation of the internal temperature). The reaction is complete after 10 h. After cooling and venting the pressure, 1 mL of sample was collected for determination of the yield and n/iso selectivity by GC analysis, to which 150 µl of isooctane was added as internal standard. The yield was 99% for the TMH ester (n/iso: >99). High-boiling products were not detected.

Methanol and traces of unreacted olefin were first removed by fractional distillation before the TMH ester was obtained in pure form. The reaction vessel used for the hydrolysis is a closable pressure tube (ACE Glass Incorporated, 5 mL). The TMH ester methyl 3,5,5-trimethylhexanoate (437.5 mg, 2.54 mmol, 500 µL) was transferred together with water (2.492 g, 0.138 mol, 2.5 mL) to the reaction vessel. 75 mg (17.1% by weight) of the heterogeneous catalysts listed in table 1 is then added. The reaction vessel is closed and placed in a preheated heating block. The reaction is carried out at 100° C. with continuous stirring (550 rpm, magnetic stirrer). After 20 hours, the reaction is terminated, the reaction vessel is taken out of the heating block and is cooled to ambient temperature. A sample to check the conversion by GC is then prepared. This is done by mixing in a GC vial 0.1 ml of the organic phase (product mixture without water and catalyst) together with 0.05 ml of isooctane as internal standard and 1 ml of acetone as solvent. The yield (Y) was then determined by GC-FID and is noted in table 7 for each catalyst.

TABLE 7

Comparison of yields (TMH acid)

| Catalyst | Yield (TMH acid) % |
|---|---|
| Z-beta-H | 44 |
| Z-beta-H-25 | 43 |
| Z-beta-H-38 | 69 |
| Z-Y-H-60 | 48 |
| Z-Y-H-80 | 50 |
| Z-beta-H-150 | 48 |

The invention claimed is:

1. A process for preparing a carboxylic acid or salt thereof, with the process comprising the following steps:
   a) preparing an ester by reacting a C2 to C20 hydrocarbon having at least one multiple bond, prefer carbon monoxide and with an alcohol A in the presence of a homogeneous catalyst system in a reaction zone to obtain a product mixture;
   b) carrying out a membrane separation to separate the homogeneous catalyst system from the product mixture, whereby the homogeneous catalyst system and unreacted hydrocarbon and/or unreacted alcohol A, are enriched in a retentate and the ester formed in step a) is enriched in a permeate, wherein the membrane material used is a membrane material capable of OSN (organic solvent nanofiltration) that includes at least one separation-active layer;
   c) separating the ester formed in step a) from the permeate in at least one separation step selected from thermal separation, extraction, crystallization and membrane separation;
   d) hydrolyzing or saponifying the ester prepared in step a) in the presence of an acidic catalyst or a saponifying agent to obtain a reaction mixture that comprises at least the carboxylic acid or salt thereof, an eliminated alcohol A, water and unreacted ester; and
   e) separating the carboxylic acid or salt thereof formed in step d) in at least one separation process step selected from thermal separation, extraction, crystallization and membrane separation.

2. The process according to claim 1, wherein the separation-active layer is composed of a PAEK (polyaryl ether ketone) polymer.

3. The process according to claim 2, wherein the separation-active layer is composed of PEEK (polyether ether ketone).

4. The process according to claim 1, wherein the alcohol A is a mono- or polyol (two or more OH groups) having 1 to 50 carbon atoms, or a mixture of two or more mono- and/or polyols.

5. The process according to claim 4, wherein the alcohol used in step a) is selected from the group consisting of methanol, ethanol, 1-propanol, 1-butanol, 1-pentanol, 1-hexanol, 2-propanol, tert-butanol, 3-pentanol, 2-propylheptanol, cyclohexanol, phenol or mixtures thereof.

6. The process according to claim 1, wherein the homogeneous catalyst system used step a) comprises at least one metal from groups 8 to 10 of the periodic table of the elements or a compound thereof, a phosphorus-containing ligand and an acid as a co-catalyst.

7. The process according to claim 1, wherein the carbon monoxide used in the reaction in step a) is provided by first separating a carbon monoxide-containing gas and passing the carbon monoxide into the reaction zone.

8. The process according to claim 1, wherein the membrane material is a membrane material capable of OSN (organic solvent nanofiltration) that is stable for at least 300 h in the presence of the acid in the catalyst system.

9. The process according to claim 6, wherein the acid in the catalyst system in step a) is a Bronsted acid having a $pKa \leq 5$, or a Lewis acid having an LAU value of more than 25.

10. The process according to claim 6, wherein the acid in the catalyst system in step a) is a Bronsted acid or a Lewis acid, the Bronsted acid being perchloric acid, sulfuric acid, phosphoric acid, methylphosphonic acid or a sulfonic acid and the Lewis acid being aluminium triflate, aluminium chloride, aluminium hydride, trimethylaluminium, tris(pentafluorophenyl)borane, boron trifluoride, boron trichloride or a mixture thereof.

11. The process according to claim 1, wherein the retentate is recycled into the reaction zone in step a) and the permeate is supplied to the subsequent step c).

12. The process according to claim 1, wherein the process after the separation in step c) includes the following further steps:
   c1) transesterifying the ester formed in step a) with a second alcohol, wherein this second alcohol differs from the alcohol used in step a), in a second reaction zone to obtain a second product mixture;
   c2) separating the ester formed in step c1) and separating the rest of the second product mixture through thermal separation and/or by means of membrane separation, and recycling the eliminated alcohol A into a first reaction zone and also recycling an unreacted second alcohol into the second reaction zone;
   wherein the ester formed in step c1) is used in the hydrolysis or saponification in step d).

13. The process according to claim 12, wherein the second alcohol in step c1) is added in excess.

14. The process according to claim 12, wherein the second alcohol used in step c1) is a more high-boiling alcohol than the first alcohol.

15. The process according to claim 12, wherein a proportion of the eliminated alcohol A is withdrawn from the second reaction zone and recycled into the reaction zone of step a).

16. The process according to claim 2, wherein the separation-active layer is composed of PEEK having a degree of sulfonation of less than 10%.

17. The process according to claim 1, wherein the alcohol A is a mono- or polyol (two or more OH groups) having 1 to 15 carbon atoms, or a mixture of two or more mono- and/or polyols.

18. The process according to claim 1, wherein the alcohol A is a mono- or polyol (two or more OH groups) having 1 to 10 carbon atoms or a mixture of two or more mono- and/or polyols.

19. The process according to claim 1, wherein the acid in the catalyst system in step a) is a Bronsted acid having a $pKa \leq 3$ or a Lewis acid having an LAU value of more than 29.

* * * * *

UNITED STATES PATENT AND TRADEMARK OFFICE
CERTIFICATE OF CORRECTION

PATENT NO. : 11,008,275 B2
APPLICATION NO. : 16/893481
DATED : May 18, 2021
INVENTOR(S) : Kucmierczyk et al.

Page 1 of 1

It is certified that error appears in the above-identified patent and that said Letters Patent is hereby corrected as shown below:

In the Claims

Column 11,
Line 22, "multiple bond, prefer carbon" should read -- multiple bond, carbon --.
Line 64, "system used step a)" should read -- system used in step a) --.

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*